United States Patent [19]

Irons et al.

[11] 4,247,452
[45] Jan. 27, 1981

[54] PURIFICATION OF PERTUSSIS HAEMAGGLUTININS

[75] Inventors: Laurence I. Irons, Salisbury; Alastair P. MacLennan, Amesbury, both of England

[73] Assignee: The Secretary of State for Defence in Her Britannic Majesty's Government of the United Kingdom of Great Britain and Northern Ireland, London, England

[21] Appl. No.: 15,467

[22] Filed: Feb. 26, 1979

[30] Foreign Application Priority Data

Mar. 1, 1978 [GB] United Kingdom ............... 8089/78

[51] Int. Cl.³ .................... A61K 39/10; C07G 7/00
[52] U.S. Cl. .................................. 260/112 R; 260/8; 260/112 B; 424/92
[58] Field of Search ............... 260/112 B, 112 R, 8; 424/92

[56] References Cited

U.S. PATENT DOCUMENTS

| 3,395,219 | 7/1968  | Millman ........................... 424/92 |
| 3,405,218 | 10/1968 | Haskell et al. .................... 424/92 |
| 3,465,078 | 9/1969  | Spiesel ............................. 424/92 |
| 4,029,766 | 6/1977  | Helting ............................ 424/92 |

OTHER PUBLICATIONS

Biochimica et Biophysica Acta, 444(1976), pp. 765–782, Arai et al.
Chem. Abstracts, vol. 78, 1973, 41239p, Sato et al.
Chem. Abstracts, vol. 85, 1976, G1201t, Morse et al., 1976.

*Primary Examiner*—Howard E. Schain
*Attorney, Agent, or Firm*—Stevens, Davis, Miller & Mosher

[57] ABSTRACT

The Leukocytosis Promoting Factor (LPF) of Bordetella Haemagglutinin (HG) is separated from crude cell supernatant or partially purified protein by affinity chromatography on a column material consisting of an insoluble polymeric support to which is bound a sialoprotein (glycoprotein containing sialic acid) or other substance rich in sialic acid.

The sialoprotein was preferably a plasma sialoprotein, such as haptoglobin or ceruloplasmin, or a salivery mucin, and the polymeric support was preferably an agarose gel, though other conventional supports could be used.

By this process, on treatment of an ammonium sulphate precipitated extract, the haemagglinating activity may be increased 300–600 fold over the extract and 10,000 times over the crude centrifuged cell supernatant. Alternatively a fraction substantially free from LPF-HG may be collected.

Pertussis LPF-HG is reported to have various useful clinical properties, in particular adjuvant effect on antigenicity and the abilities to induce leukocytosis and sensitivity to histamine. By the process of the present invention LPF-HG may be produced cheaply and in large quantities, or removed from other cell extracts.

17 Claims, 1 Drawing Figure

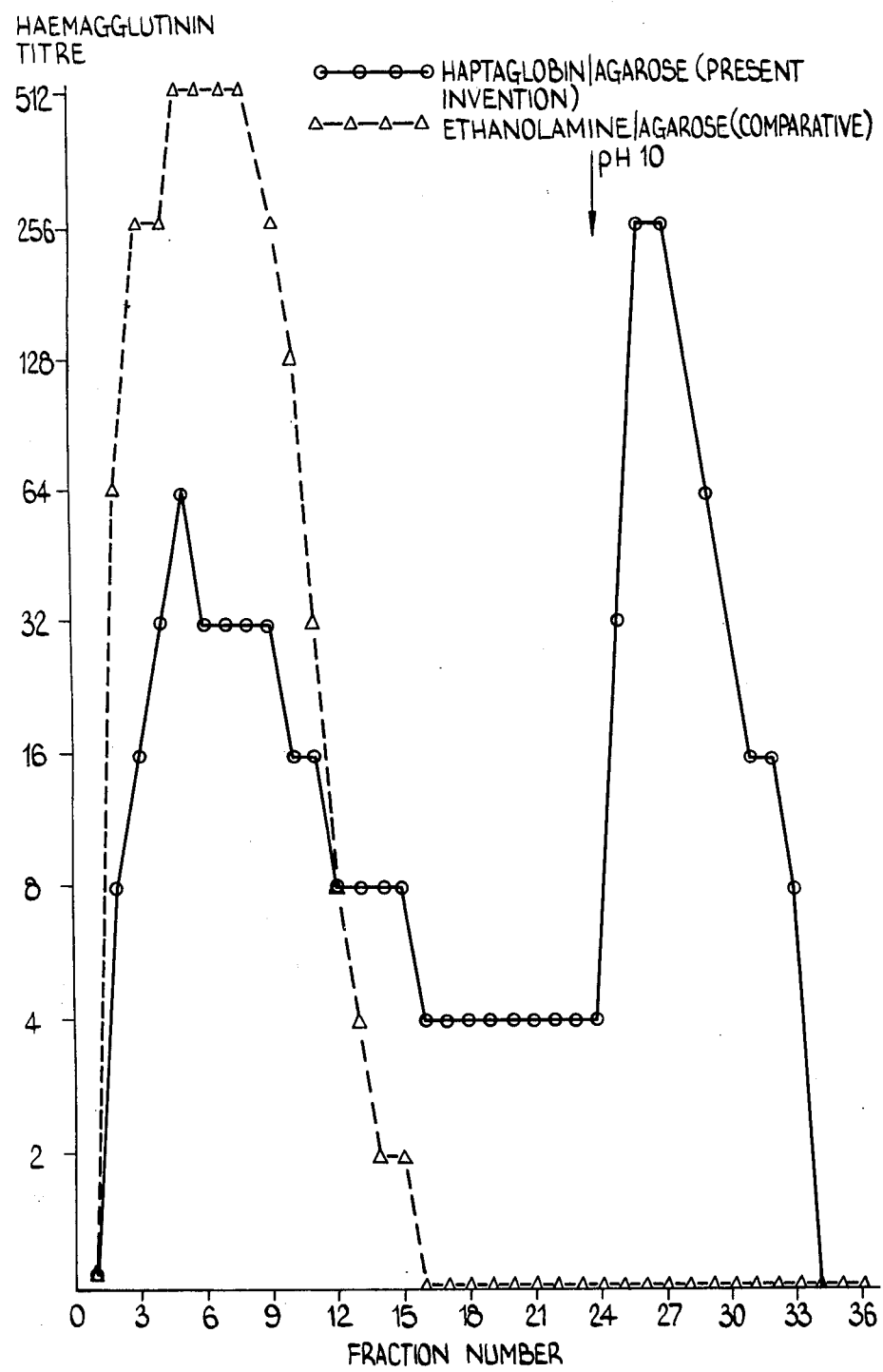

PURIFICATION OF PERTUSSIS HAEMAGGLUTININS

The invention relates to the separation of haemagglutinin from bacteria of the genus Bordetella.

Haemagglutinins are substances that can cause red cells in suspension to clump together, or agglutinate. Recent work by Arai and Sato (Biochim. Biophys. Acta 444 (1976) 765–782) and by Morse and Morse (J. exptl. Med. 143 (1976) 1483–1502) has shown that *Bordetella pertussis* organisms can produce two distinct haemagglutinins. Of these, one, the Leukocytosis Producing Factor-haemagglutinins (LPF-HG) is produced under variable conditions of culture aeration and possesses biological properties of possible clinical application, in particular an adjuvant effect on antigenicity, and the abilities to induce leukocytosis and sensitivity to histamine. The second haemagglutinin, fimbrial haemagglutinin, (F-HG), appears to be associated with the fimbriate state and its production is greatly favoured in static, poorly aerated cultures. The invention relates to the separation of LPF-HG from liquid preparations derived from bacterial cells of the genus Bordetella.

The pertussis haemagglutinins have previously been purified only by laborious and complex procedures, involving density gradient centrifugation in sucrose or caesium chloride, with consequent high cost and limited availability. It has now surprisingly been found that pertussis LPF-HG can be purified by a simple affinity chromatography method on a sialic acid-rich medium.

The invention is based on an identification of the chemical nature of the red cell surface material to which LPF-HG binds specifically. It has previously been reported that haemagglutination brought about by the influenza virus is due to a combination of the viral haemagglutinin with sialic acid-containing substances on the red cell surface. This was recognised through the observation that the addition of the enzyme neuraminidase to red cells prevents hamagglutination, and this enzyme specifically splits a sialic acid linkage. Since neuraminidase does not prevent haemagglutination by pertussis LPF-HG it has been assumed by others that sialic acid groups are not involved in the attachment of LPF-HG to the cell. On this view it must appear surprising that LPF-HG attaches to sialic acid-containing substances on a chromatographic support, by virtue of a neuraminidase-sensitive linkage.

According to the present invention, therefore, a process for the separation of LPF-HG from a liquid preparation derived from bacterial cells of the genus Bordetella, includes the step of subjecting a liquid preparation containing said LPF-HG to affinity chromatography on a stationary phase comprising an insoluble polymeric support and, bound thereto, a sialoprotein (glycoprotein containing sialic acid) or other substances rich in sialic acid. Plasma sialoproteins such as haptoglobin and ceruloplasmin are suitable but other sialoproteins such as salivary mucins could be used. The invention is especially applicable to the species *B. Pertussis* but may also be applied to other species of the genus Bordetella, which produce LPF-HG, for example *B. Bronchisepticus* and *B. Parapertussis.*

The support may be any conventional polymeric support as used for affinity chromatography, for example cellulose derivatives such as diethyl aminoethyl cellulose, cross-linked dextrans, agarose gels, polyacrylamide beads, polymerised maleic anhydride, or porous glass. The protein may be attached by covalent bonds to the support by conventional techniques, normally following cyanogen bromide activation of the support.

The liquid preparation subjected to affinity chromatography may be a simple cell extract obtained by cell disruption, preferably clarified by centrifugation. Alternatively it may be a partially purified material, for example as obtained by ammonium sulphate precipitation. For optimal retention on the column the liquid preparation containing LPF-HG should preferably be applied in a buffer solution having a pH in the range of 4–7, preferably about 6.5. The column may be washed with a similar buffer after which the LPF-HG may be eluted, for example by a change of pH to about 8 or above, preferably to about pH 10. All buffers should preferably contain sodium chloride at a concentration of about 0.2 to 1 Molar.

The process of the invention yields two factors. One, which is obtained by washing the column with buffer after the application of the liquid preparation to the column but before elution of LPF-HG, contains substantially no LPF-HG, whilst the second, which is obtained by elution with buffer of pH 8 or above, contains a product which has the properties of haemagglutinin LPF as described by Arai and Sato (Biochim Biophys Acta 444 (1976) 765–782) and appears to contain little or none of the second haemagglutinin F-HG. Therefore the method described is specific for the separation of LPF-HG from the liquid preparations derived from bacterial cells of the genus Bordetella and may be used to produce either purified LPF-HG or a substantially LPF-HG free product.

A specific embodiment of the process of the invention will now be described by way of example only, with reference to the accompanying graph FIG. 1, which shows haemagglutinin titres of successive eluent fractions as explained below.

EXAMPLE 1

Bacteria of the "Tohama" strain of *Bordetella pertussis* (available from the Japanese Federation of Culture Collections of Micro-organisms) were grown at 37° C., with aeration by shaking, for up to 5 days in the liquid medium described by Cohen & Wheeler, Amer. Journal Public Health Vol 36 (1946) p 371. The cells were separated from the medium by centrifugation and the cell paste stored at −20° C. The cell paste was suspended in 0.01 M Tris-0.005 M $MgCl_2$-0.145 M NaCl-0.015 M $NaN_3$ buffer (pH 7.4) at a concentration of about 12% (w/v) and mechanically disintegrated in a mechanical glass bead disintegrator ("Dyno-Mill" Trade Mark). The suspension was centrifuged at 10,000 g for 30 minutes and the supernatant again centrifuged at 360,000 g for 90 minutes. Ammonium sulphate was added to the supernatant to 50% (w/v) and the mixture allowed to stand at 4° C. for 16 hours. The precipitate was removed by centrifuging at 10,000 g for 30 minutes and extracted several times with small volumes of 0.05 M Tris-0.5 M NaCl buffer (pH 8). Extracts containing haemagglutinating activity were pooled and dialysed against the Tris-NaCl pH 8 buffer. The solution obtained was then dialysed against 0.05 M phosphate 0.5 M NaCl (pH 6.5) and finally stored at 4° C. This solution which was used for further purification of the haemagglutinin will be referred to subsequently as Pertussis extract.

PREPARATION OF AFFINITY ADSORBENT 5 g of CN-Br activated agarose gel (trade mark "Sepharose 4B"—supplied by Pharmacia Fine Chemicals) was swollen and washed with 1 l of 1 mM-HCl. 15 mg of purified human haptoglobin prepared by the method of Connel and Shaw (Can. J Biochem 39 (1961) p 1013) was dissolved in 10 ml of 0.1 M $NaHCO_3$-0.5 M NaCl buffer (pH 8.3) and added to the washed CN-Br agarose gel. The suspension was mixed end over end at 23° C. for 3 hours. The suspension was filtered, washed with the bicarbonate buffer (90 ml) and transferred to 100 ml of 1 M ethanolamine-borate-0.5 M NaCl buffer (pH 9) for 2 hours at room temperature. The gel was washed 5 times with alternative washes of borate-0.5 M NaCl pH 8.1 and 0.1 M acetate-0.5 M NaCl pH 3.8 buffers. The gel was stored at borate-NaCl (pH 8.1) buffer at 4° C. Analysis of the supernatant obtained after the protein coupling reaction showed that all the added haptoglobin was bound to the CN-Br Sepharose. For purpose of comparison, CN-Br-activated Sepharose 4B was also treated with ethanolamine by the same procedure to give deactivated agarose gel containing ethanolamine groups and no haptoglobin.

PURIFICATION OF PERTUSSIS EXTRACT

A 3 ml sample of the Pertussis extract containing haemagglutinating activity of about 200 units/mg (one unit of haemagglutinating activity is defined as the reciprocal of the highest dilution of the sample causing complete agglutination of 0.05 ml of chicken or goose erythrocytes in phosphate buffered saline pH 7.2 when measured by a micro-titre method) was applied to a 2×1 cm column of affinity adsorbent prepared as described above and washed onto the column with 0.05 M phosphate-0.5 M NaCl buffer (pH 6.5). Successive 0.5 ml fractions were collected and assayed for haemagglutinin titre. The results are shown in FIG. 1. Overall about 50% of the applied activity was retained by the adsorbent. Substantially all this retained activity was eluted following a change to 0.1 M Tris-0.5 M NaCl buffer (pH 10) at fraction 24 (see FIG. 1).

The process was repeated using the ethanolamine-deactivated agarose. Virtually no haemagglutinin was retained by the column or eluted by the change in pH (FIG. 1).

Fractions containing haemagglutinating activity eluted by the pH 10 buffer were pooled and concentrated by vacuum dialysis against 0.05 M Tris-0.5 M NaCl buffer (pH 8) to about 400 μg protein/ml. The specific haemagglutinating activity of the concentrated solution was about 60,000–120,000 units/mg and 6000–8000 units/mg when measured with goose and chicken erythrocytes respectively. This represents a 300–600 fold purification of the haemagglutinin from the Pertussis extract and about a 10000 fold purification from the supernatant obtained after the initial cell disintegration and centrifugation. About 1–2 mg of purified haemagglutinin was obtained from 30 ml of Pertussis extract containing 50 mg protein/ml.

In 12.5% acrylamide gels containing sodium dodecyl sulphate (SDS) the purified haemagglutinin showed 5 main bands of about equal intensity and a few faint minor ones (FIG. 2). The molecular weights of the major bands estimated from the mobilities of the marker proteins in the gel system used were: 27,200, 24,000, 22,400, 21,100 and 12,600 (average of 8 determinations). The purified haemagglutinin hardly penetrated gels without SDS at neutral or alkaline pH. However in 5% acrylamide gels at pH 4.3 it gave a major band with a mobility relative to the tracker dye of 0.5–0.6 and also a minor band near the origin of the gels.

Electron microscopy of the haemagglutinin in Tris-NaCl pH 10 buffer showed the predominant structure to consist of roughly spherical particles of diameter about 60 A°. These tended to form aggregates so that individual structures could not be seen. Some preparations also contained a very small number of filamentous structures of diameter about 30 A° and of variable length (1250–2250 A°).

Gel filtration of the Pertussis extract on agarose gel (Sepharose 6B) produced two peaks with haemagglutinating activity. The first smaller peak had an elution volume near to that of ferritin whilst the second had an elution volume greater than that of bovine albumin. Total recovery of haemagglutinating activity was about 70%. When the process was repeated with the purified material only the second peak was observed and there was considerable loss of activity, only 10–15% being recovered.

The biological properties of the purified haemagglutinin are shown in Table 1. It was a potent inducer of leukocytosis and injection of 0.02 μg in CF-1 mice caused 3 days later a 2 fold increase in total white blood cell counts. It also had a high histamine sensitising activity in NIH mice and injection of 0.03–0.05 μg sensitised 50% of the mice to the lethal effect of 1 mg histamine.

TABLE 1

| | Type of activity | |
|---|---|---|
| | 60000–120000 U/mg (goose cells) | |
| | 6000–8000 U/mg (chicken cells) | |
| Haemagglutination LPF Activity[1] | μg injected/mouse | White Blood Cell Counts × $10^{-3}$/mm$^3$ |
| | zero | 3.4 |
| | 0.02 | 8.5 |
| | 0.1 | 5.9 |
| | 0.5 | 10.0 |
| | 1.0 | 19.5 |
| | 2.0 | 35.9 |
| Histamine Sensitising Activity | SD50 (NIH mice)[2] 0.03–0.05μg | |

[1]Groups of 5 CF-1 mice were injected intravenously and white blood cell counts were performed 3 days later.
[2]50% sensitising dose for histamine lethality in NIH mice.

These results clearly indicate that the purified haemagglutinin corresponds to the haemagglutinin LPF described by Arai and Sato.

To investigate the site of binding to the haptoglobin, about 2 ml of the affinity adsorbent in the borate/NaCl pH 8.1 buffer was centrifuged and the gel washed 4 times with 0.1 M acetate buffer pH 5.0. 0.4 ml of neuraminidase (Cl. perfringens enzyme, 1 mg/ml in acetate buffer) was added to the washed gel and the total volume made to about 4 ml with acetate buffer. The suspension was incubated at 37° C. for 4 hours. A second 2 ml sample of haptoglobin-agarose was treated in the same way but omitting the neuraminidase (buffer-washed adsorbent). 2×1 cm columns of buffer washed adsorbent (A) neuraminidase treated adsorbent (B), untreated adsorbent (C) and ethanolamine-agarose (D) were poured and washed with 0.05 M phosphate-0.5 M NaCl pH 6.5 buffer. 0.4 ml aliquots of a Pertussis extract with haemagglutinin titre 256, previously dialysed against the pH 6.5 buffer, were applied to each column.

The columns were washed with phosphate pH 6.5 buffer and 10 drop fractions collected. At fraction 15 the buffer was changed to 0.1 M Tris-0.5 M NaCl pH 10 buffer and 10 more fractions collected. The haemagglutinin titres of all fractions were measured with goose erythrocytes and are shown in Table 2. The volume per fraction for fractions 17 to 24 was 0.55 ml. Total haemagglutinating activity recovered in fractions 17–24 from A, B, C and D were 836, 594, 814 and zero units respectively. The yield of purified LPF obtained from A, B and C was 9.3, 6.6 and 9.0 μg respectively, assuming LPF has a specific haemagglutinating activity of 90,000 units/mg. This shows that after neuraminidase treatment of haptoglobin-Sepharose, which removes protein bound sialic acid groups, the yield of purified LPF is reduced by about 28%. This reduction is somewhat less than might be expected due, no doubt, to some factor such as poor availability of substrate to the enzyme, but still indicates the role of sialic acid in LPF binding.

TABLE 2

| FRACTION | HAEMAGGLUTIN TITRES | | | |
|---|---|---|---|---|
| | A | B | C | D |
| 1 | 0 | 2 | 0 | 2 |
| 2 | 32 | 32 | 32 | 64 |
| 3 | 16 | 16 | 16 | 64 |
| 4 | 8 | 8 | 8 | 32 |
| 5 | 8 | 8 | 2 | 32 |
| 6 | 2 | 4 | 2 | 8 |
| 7 | 0 | 4 | 2 | 4 |
| 8 | 0 | 2 | 0 | 2 |
| 9 | 0 | 2 | 0 | 2 |
| 10 | 0 | 2 | 0 | 2 |
| 11 | 0 | 2 | 0 | 0 |
| 12 | 0 | 2 | 0 | 0 |
| 13 | 0 | 2 | 0 | 0 |
| 14 | 0 | 0 | 0 | 0 |
| 15 | 0 | 0 | 0 | 0 |
| 16 | 0 | 0 | 0 | 0 |
| 17 | 6 | 8 | 2 | 0 |
| 18 | 16 | 16 | 16 | 0 |
| 19 | 16 | 16 | 16 | 0 |
| 20 | 16 | 4 | 16 | 0 |
| 21 | 8 | 2 | 8 | 0 |
| 22 | 6 | 2 | 8 | 0 |
| 23 | 6 | 2 | 4 | 0 |
| 24 | 2 | 2 | 4 | 0 |

We claim:

1. A process for the separation of LPF-HG from a liquid preparation derived from bacterial cells of the genus Bordetella, said process consisting of,
   preparing a column of a stationary phase comprising an insoluble polymeric support and, bound thereto, a substance rich in sialic acid,
   applying said liquid preparation to said stationary phase to cause said LPF-HG to bind thereto, and washing said stationary phase to obtain a liquid preparation substantially free of LPF-HG.

2. A process according to claim 1 wherein the LPF-HG is eluted from said stationary phase with an eluting medium.

3. A process according to claim 1 wherein the bacterial cells are of a species selected from the group consisting of Bordetella Pertussis, B. Bronchisepticus and B. Parapertussis.

4. A process according to claim 1 wherein the substance rich in sialic acid is a sialoprotein.

5. A process according to claim 4 wherein the sialoprotein is selected from plasma sialoproteins and salivary mucins.

6. A process according to claim 5 wherein the plasma sialoprotein is one of haptoglobin and ceruloplasmin.

7. A process according to claim 1 wherein the insoluble polymeric support is selected from the group consisting of agarose gel, diethyl aminoethyl cellulose, crossed linked dextrans, polyacrylamide beads, polymerised maleic anhydride and porous glass.

8. A process according to claim 1 wherein the insoluble polymeric support is activated with cyanogen bromide prior to the attachment of a substance rich in sialic acid to said support.

9. A process according to claim 1 wherein the liquid preparation containing LPF-HG is obtained by a process including the step of ammonium sulphate precipitation of haemagglutinin-containing material from the cell extract.

10. A process according to claim 1 wherein the liquid preparation containing LPF-HG is buffered to a pH between 4 and 7 before contact with the stationary phase.

11. A process according to claim 10 wherein the liquid preparation is buffered to a pH of about 6.5.

12. A process according to claim 10 wherein the buffer solution contains sodium chloride.

13. A process according to claim 12 wherein the concentration of sodium chloride in the buffer solution is between 0.2 and 1 Molar.

14. A process according to claim 2 wherein the LPF-HG is eluted from the stationary phase by an eluting medium comprising a buffer solution having a pH of 8 or above.

15. A process according to claim 14 wherein buffer solution has a pH of about 10.

16. A process according to claim 14 wherein the buffer solution contains sodium chloride.

17. A process according to claim 16 wherein the concentration of sodium chloride in the buffer solution is between 0.2 and 1 Molar.

* * * * *

UNITED STATES PATENT AND TRADEMARK OFFICE
CERTIFICATE OF CORRECTION

PATENT NO. : 4,247,452

DATED : January 27, 1981

INVENTOR(S) : Laurence I. Irons

It is certified that error appears in the above–identified patent and that said Letters Patent are hereby corrected as shown below:

On the face of the patent, the Assignee should read as follows:

---Secretary of State for Social Services in Her Britannic Majesty's Government of the United Kingdom of Great Britain and Northern Ireland, London, England---

Signed and Sealed this

Second Day of June 1981

[SEAL]

Attest:

RENE D. TEGTMEYER

*Attesting Officer*  *Acting Commissioner of Patents and Trademarks*